(12) United States Patent
Hillen

(10) Patent No.: US 11,553,874 B2
(45) Date of Patent: Jan. 17, 2023

(54) DENTAL IMAGE FEATURE DETECTION

(71) Applicant: VideaHealth, Inc., Cambridge, MA (US)

(72) Inventor: Florian Hillen, Cambridge, MA (US)

(73) Assignee: VideaHealth, Inc., Cambridge, MA (US)

( * ) Notice: Subject to any disclaimer, the term of this patent is extended or adjusted under 35 U.S.C. 154(b) by 0 days.

(21) Appl. No.: 17/691,894

(22) Filed: Mar. 10, 2022

(65) Prior Publication Data
US 2022/0192590 A1 Jun. 23, 2022

Related U.S. Application Data

(63) Continuation of application No. 17/196,888, filed on Mar. 9, 2021, which is a continuation of application
(Continued)

(51) Int. Cl.
*A61B 5/00* (2006.01)
*G06N 3/08* (2006.01)
(Continued)

(52) U.S. Cl.
CPC .......... *A61B 5/4547* (2013.01); *A61B 5/7267* (2013.01); *A61B 5/743* (2013.01);
(Continued)

(58) Field of Classification Search
CPC ..... A61B 5/4547; A61B 5/743; A61B 5/7267; A61B 5/7475; G06K 9/6256; G06N 3/08;
(Continued)

(56) References Cited

U.S. PATENT DOCUMENTS

2006/0122467 A1 6/2006 Harrington et al.
2010/0279248 A1 11/2010 Mourad et al.
(Continued)

OTHER PUBLICATIONS carestreamdental.com [online], "Logicon Caries Detector Software Version 5.2," Carestream Dental, 2019, retrieved on May 5, 2019, retrieved from URL <https://www.carestreamdental.com/en-us/products/imaging-software/logicon-caries-detector-software/>, 4 pages.
(Continued)

*Primary Examiner* — Amelie R Davis
(74) *Attorney, Agent, or Firm* — Fish & Richardson P.C.

(57) ABSTRACT

A system includes a computing device that includes a memory configured to store instructions. The system also includes a processor to execute the instructions to perform operations that include receiving data representing one or more images of dental information associated with a patient. Operations include adjusting the data representing the one or more images of dental information into a predefined format, wherein adjusting the data includes adjusting one or more visual parameters associated with the one or more images of dental information. Operations include using a machine learning system to determine a confidence score for one or more portions of the one or more images of dental information, and producing a representation of the determined confidence scores to identify one or more detected features present in the one or more images of dental information.

19 Claims, 11 Drawing Sheets

Related U.S. Application Data

No. 16/387,388, filed on Apr. 17, 2019, now abandoned.

(60) Provisional application No. 62/658,675, filed on Apr. 17, 2018.

(51) Int. Cl.
| | |
|---|---|
| *G16H 30/40* | (2018.01) |
| *G06T 7/00* | (2017.01) |
| *G06K 9/62* | (2022.01) |
| *G16H 50/20* | (2018.01) |
| *G06N 20/00* | (2019.01) |

(52) U.S. Cl.
CPC .......... *A61B 5/7475* (2013.01); *G06K 9/6256* (2013.01); *G06N 3/08* (2013.01); *G06N 20/00* (2019.01); *G06T 7/0014* (2013.01); *G16H 30/40* (2018.01); *G16H 50/20* (2018.01); *G06T 2207/20081* (2013.01); *G06T 2207/30036* (2013.01); *G06T 2207/30096* (2013.01)

(58) Field of Classification Search
CPC .................. G16H 30/40; G06T 7/0014; G06T 2207/20081; G06T 2207/30096; G06T 2207/30036
See application file for complete search history.

(56) References Cited

U.S. PATENT DOCUMENTS

| | | |
|---|---|---|
| 2013/0215388 A1 | 8/2013 | Imamura |
| 2016/0225151 A1* | 8/2016 | Cocco ..................... H04N 7/18 |
| 2017/0086943 A1 | 3/2017 | Mah |
| 2017/0169562 A1 | 6/2017 | Somasundaram et al. |
| 2017/0343481 A1 | 11/2017 | Jahanshahi et al. |
| 2018/0028294 A1* | 2/2018 | Azernikov ............. G06V 10/82 |
| 2018/0325484 A1 | 11/2018 | Patel |
| 2018/0342060 A1 | 11/2018 | Yao et al. |
| 2019/0122073 A1 | 4/2019 | Ozdemir et al. |
| 2019/0205703 A1 | 7/2019 | Duesterwald et al. |
| 2019/0313963 A1 | 10/2019 | Hillen |
| 2021/0353216 A1 | 11/2021 | Hillen |

OTHER PUBLICATIONS

International Preliminary Report on Patentability in International Application No. PCT/US2019/027988, dated Oct. 20, 2020, 8 pages.
International Search Report and Written Opinion in International Appln. No PCT/US2019/027988, dated Jul. 16, 2019, 15 pages.
Kantor et al., "A clinical comparison of X-ray films for detection of proximal surface caries," Journal of the American Dental Associates, Dec. 1985, 111(6):967-969.
Konecny et al., "Federated Learning: Strategies for Improving Communication Efficiency," 2016, retrieved on Oct. 30, 2017, retrieved from URL <http://arxiv.org/abs/1610.05492>, 10 pages.
Lee et al., "Detection and diagnosis of dental caries using a deep learning-based convolutional neural network algorithm," Journal of Dentistry, 2018, pp. 1-6.
pinnaclecare.com [online], "The Human Cost and Financial Impact of Misdiagnosis," PinnacleCare, 2016, retrieved from URL <www.pinaclecare.com/info/misdiagnosis/>, 2 pages.
Ronneberger et al., "U-Net: Convolutional Networks for Biomedical Image Segmentation," Medical Image Computing and Computer-Assisted Intervention—MICCAI 2015, Lecture Notes in Computer Science, 18 pages.
Shah et al., "Recent advances in imaging technologies in dentistry," World J Radiol, 2014, 6:794-807.
Srivastava et al., "Detection of tooth caries in bitewing radiographs using deep learning," Parallel Dots, 2017, 3 pages.
Ali et al., "Detection and Classification of Dental Caries in X-ray Images Using Deep Neural Networks," ICSEA 2016: The Eleventh International Conference on Software Engineering Advances, 2016, pp. 223-227.

* cited by examiner

DENTAL IMAGE FEATURE DETECTION

RELATED APPLICATIONS

This application is a continuation application and claims priority to U.S. application Ser. No. 17/196,888, filed on Mar. 9, 2021, which is a continuation application and claims priority to U.S. application Ser. No. 16/387,388, filed on Apr. 17, 2019, which claims priority to U.S. Provisional Application No. 62/658,675, filed on Apr. 17, 2018. The contents of which are hereby incorporated by reference.

BACKGROUND

This description relates to using machine learning methods to analyze and detect features, i.e. dental pathologies, in (dental) radiographs.

Dental radiographs are one diagnostic tool in dentistry. Dentists may have limited training in reading radiographs and little support from e.g. an additional radiological department, assisting them in their diagnosis. Due to such large volume of radiograph data and limited analysis time, false negative and false positive errors may occur and could potentially lead to health risks and increased health costs due to missed detection or false treatment.

SUMMARY

The described systems and techniques can aid dental clinicians in their ability to interpret dental images, including but not limited to intra-extra oral radiographic imaging (e.g. bitewing and periapical radiographs), extra-oral radiographic imaging (e.g. panoramic x-ray), computed tomography scan (CT-scans) coming from a CT scanner, Positron emission tomography scan (PET-scans) coming from a Positron emission tomography-computed tomography scanner and Magnetic resonance imaging (MRI) scans coming from a MRI scanner, to correctly identify pathological lesions. By highlighting the potential features of interest, including but not limited to potential suspicious radiolucent lesions and potential carious lesions (also called cavities) and other pathological areas, the viewer of the radiograph can quickly recognize these detected features to reduce the number of missed lesions (false negatives) and wrongly identified lesions (false positives). By employing machine learning techniques and systems to analyze radiographs, which are presentable on displays, electronic or printed reports, etc., an evaluation of patient health condition can be efficiently provided, thereby allowing the dental professional to make an informed decision about treatment decisions. While many methodologies can be employed for pathology detection in dentistry, artificial intelligence techniques, such as deep learning algorithms, can exploit such radiographs, the images information, for training and evaluation in an effective way. By developing such techniques, the diagnostic errors in dentistry can be reduced, pathologies can be detected earlier, and the health of the patients can be improved.

In one aspect, a computing device implemented method includes receiving data representing one or more images of dental information associated with a patient. The method also includes adjusting the data representing the one or more images of dental information into a predefined format. Adjusting the data includes adjusting one or more visual parameters associated with the one or more images of dental information. The method also includes using a machine learning system to determine a confidence score for one or more portions of the one or more images of dental information, and producing a representation of the determined confidence scores to identify one or more detected features present in the one or more images of dental information.

Implementations may include one or more of the following features. The method may further include transferring data representative of the one or more images of dental information associated with the patient to one or more networked computing devices for statistical analysis. The machine learning system may employ a convolution neural network. The machine learning may be trained with dental imagery and associated annotations. One or more annotations may be produced for each of the images of dental information. The one or more detected features may include a radiolucent lesion or an opaque lesion. The produced representation may include a graphical representation that is presentable on a user interface of the computing device. The produced representation may be used for a diagnosis and treatment plan. An alert or recommendation may be produced by using the produced representation for the diagnosis and treatment plan.

In another aspect, a system includes a computing device that includes a memory configured to store instructions. The system also includes a processor to execute the instructions to perform operations that include receiving data representing one or more images of dental information associated with a patient. Operations also include adjusting the data representing the one or more images of dental information into a predefined format. Adjusting the data includes adjusting one or more visual parameters associated with the one or more images of dental information. Operations also include using a machine learning system to determine a confidence score for one or more portions of the one or more images of dental information, and producing a representation of the determined confidence scores to identify one or more detected features present in the one or more images of dental information.

Implementations may include one or more of the following features. Operations may further include transferring data representative of the one or more images of dental information associated with the patient to one or more networked computing devices for statistical analysis. The machine learning system may employ a convolution neural network. The machine learning may be trained with dental imagery and associated annotations. One or more annotations may be produced for each of the images of dental information. The one or more detected features may include a radiolucent lesion or an opaque lesion. The produced representation may include a graphical representation that is presentable on a user interface of the computing device. The produced representation may be used for a diagnosis and treatment plan. An alert or recommendation may be produced by using the produced representation for the diagnosis and treatment plan.

In another aspect, one or more computer readable media storing instructions that are executable by a processing device, and upon such execution cause the processing device to perform operations that include receiving data representing one or more images of dental information associated with a patient. Operations also include adjusting the data representing the one or more images of dental information into a predefined format. Adjusting the data includes adjusting one or more visual parameters associated with the one or more images of dental information. Operations also include using a machine learning system to determine a confidence score for one or more portions of the one or more images of dental information, and producing a representation of the determined confidence scores to identify one or more detected features present in the one or more images of dental information.

Implementations may include one or more of the following features. Operations may further include transferring data representative of the one or more images of dental information associated with the patient to one or more networked computing devices for statistical analysis. The machine learning system may employ a convolution neural network. The machine learning may be trained with dental imagery and associated annotations. One or more annotations may be produced for each of the images of dental information. The one or more detected features may include a radiolucent lesion or an opaque lesion. The produced representation may include a graphical representation that is presentable on a user interface of the computing device. The produced representation may be used for a diagnosis and treatment plan. An alert or recommendation may be produced by using the produced representation for the diagnosis and treatment plan.

These and other aspects, features, and various combinations may be expressed as methods, apparatus, systems, means for performing functions, program products, etc.

Other features and advantages will be apparent from the description and the claims.

DETAILED DESCRIPTION

Figure 1:
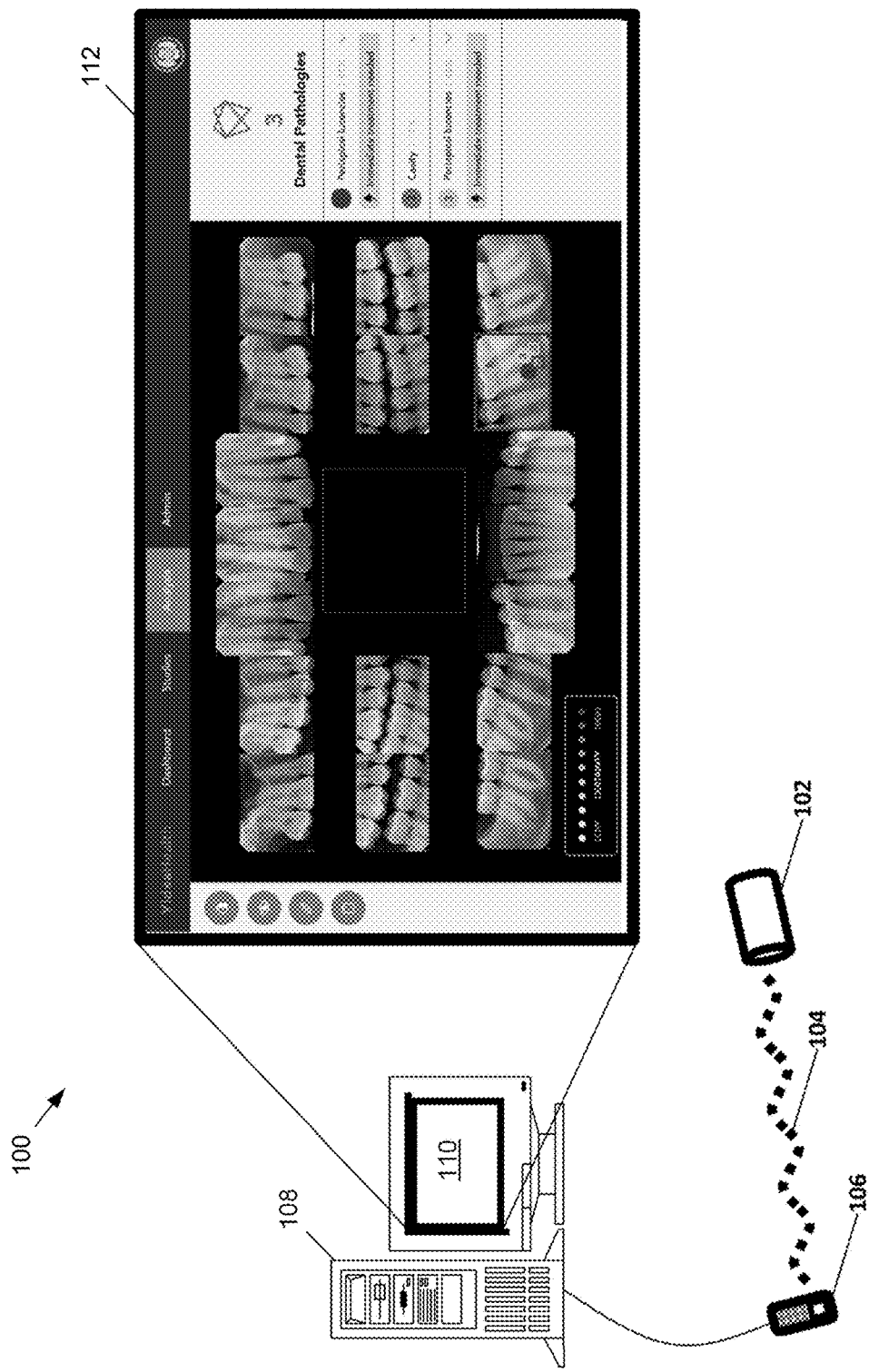
FIG. 1 illustrated the integration of the software into the work station of a dental professional.

Referring to FIG. 1, a dental analysis system 100 includes an imaging machine, 102, e.g. an x-ray machine, which emits x-ray beams, 104, to an x-ray sensor, 106 (e.g., an intra-oral sensor, an extra-oral sensor, etc.) for taking radiographic images of the jaw and teeth of a patient. The x-ray sensor 106 is connected to a computing device (e.g., a computer system 108) including a display 110 capable of presenting radiograph information for review and study for the user of the dental analysis system, including but not limited to dental professionals (e.g. general dentists, endodontists, maxilla-facial surgeons), hygienists and other radiologists. One or more techniques, formats, etc. may be used to provide the radiographic data to the computer system 108; for example, the radiograph can be provided in a raw image data-format which will be processed by a sensor-specific software into digital imaging and communications in medicine (DICOM) or any other image format (tif, png, jpg etc.) by the computer system. The computer system 108 may also execute operations so one or more artificial intelligence techniques can be used to analyze this data and present results. In some environments, the computer system 108 can provide the data to other computing devices (e.g., a cloud computing system, service, etc.) to initiate a more distributed processing of the data. The machine learning techniques and other processes of the data utilize the dental image and associated dental image information, e.g., the age and gender of the subject, i.e. the patient, when the image was taken and other image meta-data such as x-ray sensor and model used, and other potential DICOM tags which do not constitute as personal health information. Once processed, analyzed data from the artificial intelligence techniques can be returned to the computer system 108 for presentation and review (e.g., by a dental professional). The analyzed data of the dental image can be used in many ways: First, one or more presentation techniques may be employed by the computer system 108 to present the analyzed data; for example various types of user interfaces as one exemplified in interface 112 on the monitor 110, graphical representations, etc., may be used to efficiently present the data and quickly alert the professional to potential areas of interest signaling on the monitor 110 potential detected features which need immediate attention by the user. Detected features in the dental images may include radiolucent lesions, opaque lesions, other potential pathological lesions such as tooth-related radiolucent lesions, all types carious lesions, all kinds of periapical radiolucent lesions (including but not limited to cysts, infections etc.), bone fractures, tumors, osteonecrosis, other dental pathologies or obvious seemingly pathological radiolucent image parts and other features such as teeth and teeth-position/numbering, missing teeth, wisdom teeth, crowns, bridges, implants, and other anatomical characteristics such as bone density, height, width of the bones and angles, positioning, distances etc. between different facial structures (e.g. sinuses), tissues, gum and bone structures (e.g. implant and other treatment planning), margin tracing (e.g. if crowns are accurately placed on the tooth) and other assessments. Second, the analyzed data, can provide an assessment of the dental image quality, e.g., create signals indicating that the dental image is not of high enough quality (e.g., blurry or the teeth structures are overlapping), and that an algorithmic analysis or a manual analysis by a user is not optimal, and can recommend taking another dental image. Third, the analyzed data can also be employed in a workflow such as being not visualized but instead (e.g., the area, the tooth number of the detected features, carious lesions on the dental image, etc.) can be compared to the diagnosis of the user as it is being input into, e.g., practice management software using, e.g., an API between the dental software system and such practice management software. If, the assessment of the user, e.g., location (tooth number and position) and/or type of detected feature, is not the same than the analyzed data, the dental analysis system can send one or more notifications to the user regarding the event. Furthermore, by mapping the analyzed data to the associated data of the practice management system, the analyzed data can use time-series analysis and identify the progress (e.g., the health condition of a patient over period of time). Through such operations, the patient, user of the system, etc. are provided better information about potential diagnosis and treatment recommendations.

In one implementation, the dental analysis system cannot only be used prospectively but also retrospectively such as by analyzing retrospectively data, e.g., patient records of a dental practice and hospital and matching it with the analyzed diagnoses and treatment recommendations of the record, e.g., in the practice management system or the electronic health record, to estimate the quality of the dental practice and analyze if a potential recall of patients is necessary as dental features, e.g., carious lesions or other pathologies, have been missed.

The dental analysis system can also provide information such as transactional information to a payor, e.g., the health insurance, when submitting a claim. By algorithmically detecting features on the dental image and associated dental image information, the system may provide a probability factor that the diagnosis and recommended treatment of the dentist is accurate and thereby help the payor to detect various types of events (e.g., potential fraud) and conduct any additional analysis.

Upon one or more features being detected from a representation of the analyzed data, the detected features can assist in the execution of several functions such as 1) an assistive tool for the user, e.g., the dentist, to support his or her diagnosis and reduce false positive and false negative errors, 2) as a second opinion to a patient regarding their health conditions and to provide transparency to the diagnosis of the user, the dentist, the patient, etc. or 3) as an education tool for continuing education of dental professionals, dental students, etc.

The imaging machine, 102, which emits x-ray beams, 104, to an x-ray sensor, 106 can be part of an intra-extra oral radiographic imaging machine (e.g. that produces bitewing and periapical radiographs), an extra-oral radiographic imaging machine (e.g. that produces panoramic x-ray), a dental cone beam computed tomography scan machine for CT-scans coming from a CT scanner (also called a CBCT-scanner), not radiology-emitting machines such as Positron emission tomography scan (PET-scans) coming from a Positron emission tomography-computed tomography scanner, Magnetic resonance imaging (MRI) scans coming from a MRI scanner, etc.

Figure 2:
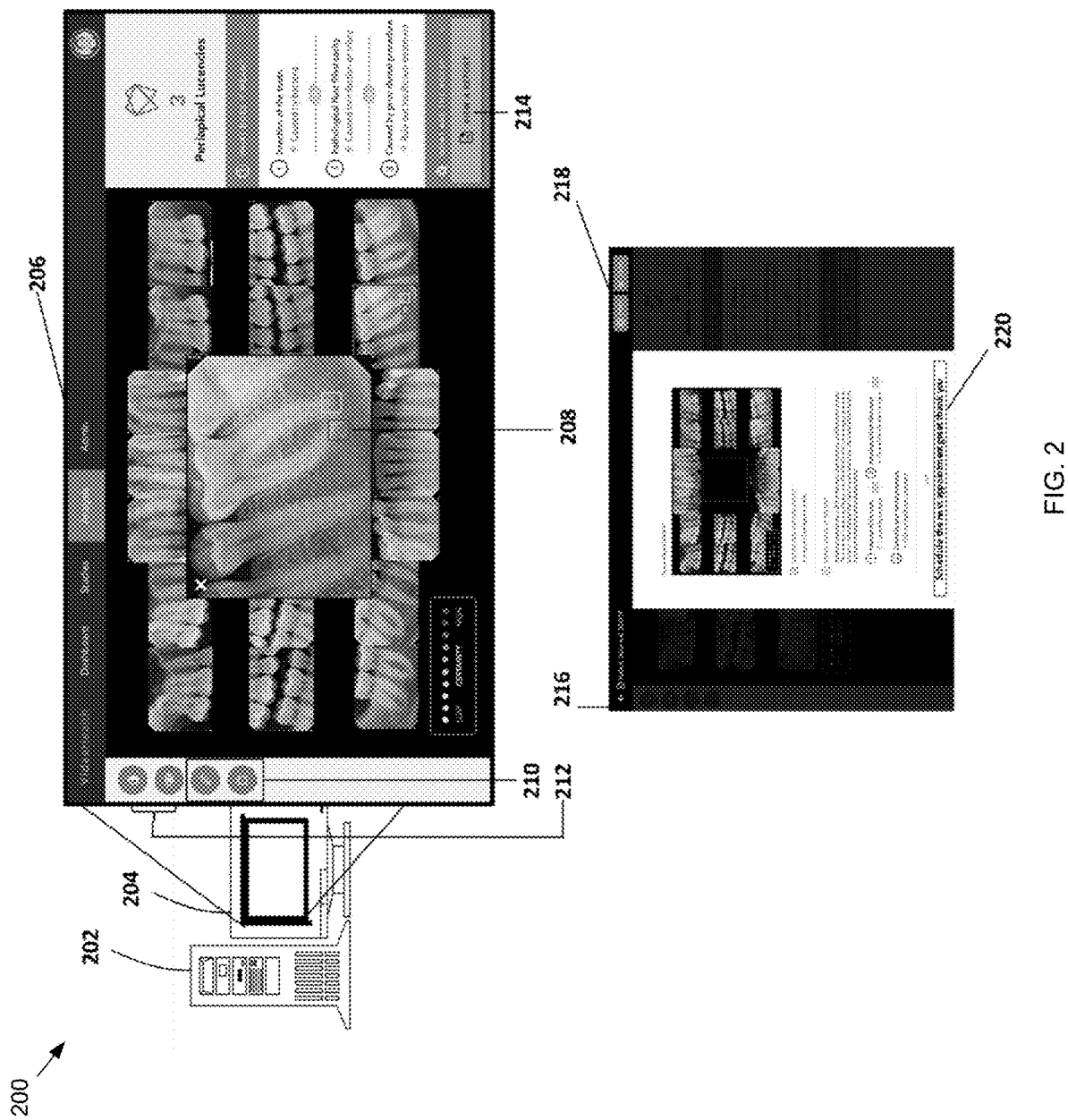
FIG. 2 illustrates functionalities of the artificial intelligence based detection system.

Referring to FIG. 2, a computing environment 200 is presented that included a computer system 202, that the user might interact with to view any software output on a display, 204. In an illustrated example, the software user-interface, 206, is presented (e.g. as requested by the user or automatically presented after a radiographic image is taken). In this example, the detected features are displayed using a colored bounding box 208 that surrounds the detected feature. In one arrangement of this user-interface, the colored box translates to a certainty score, which is decoded in colors, e.g. from green (low confidence) to red (high confidence), that the detected feature is indeed a detected feature. In an arrangement, functionalities of this software interface, 206, include user selectable icons 210 for executing various function such as deleting and adding detected features. The user can either add detected features to the radiograph in case the users suggests that the algorithm missed a detected feature, or he can delete the detected features of the algorithm, e.g. 208. In one implementation, the computing environment 200 is a dental analysis system that a user can provide feedback about the detected features, for example, by either "agreeing", "disagreeing", "clinically validated", "clinically unvalidated". The input of the user can then be used for additional training data to further improve operations of the machine learning system. After carefully reviewing the radiograph using e.g. functionalities such as contrast change, hiding the algorithmic suggestions and inversion 212, the user can generate a report 214 that automatically summaries the algorithmic findings, answers generic questions to what the detected features mean for the health of the patient, what treatment recommendations usually are given and gives the user an way to communicate to the receiver, e.g. patient or other types of information, recommendations, etc. for his review. The report, 216, can be printed, send via email or transferred by employing one or more other techniques in any other way to the receiver as provided by selectable icons 218. Furthermore, another selectable button, 220, allows the receiver to easily communicate to the user (e.g., to schedule a follow-up appointment for further treatment or diagnosis, ask questions, etc.). This feature should allow the patient to not miss any important diagnostics or treatment due to a lack for effective follow-up.

Figure 3:
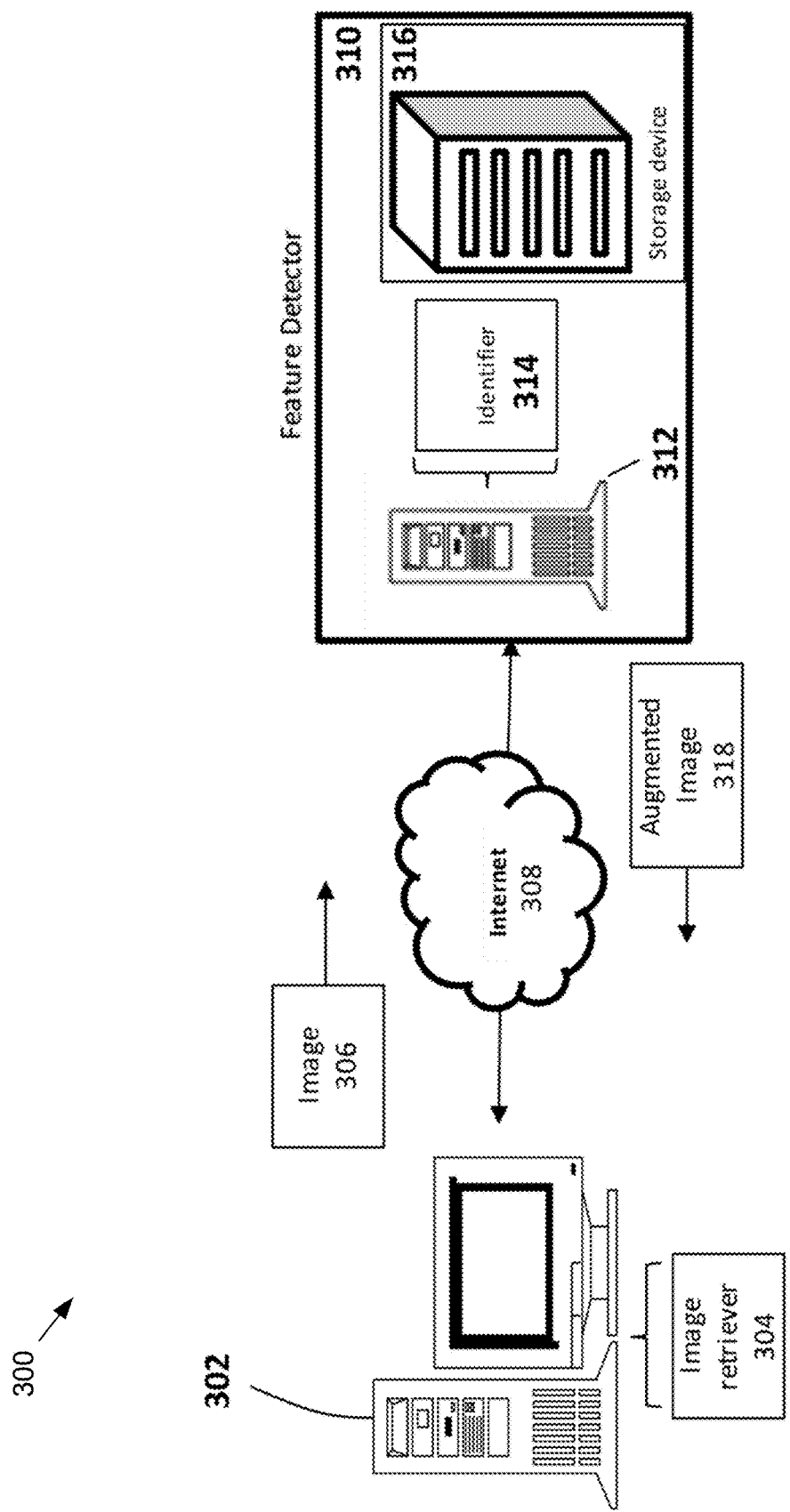
FIG. 3 is a block diagram of an internet-based computer network to provide the detected features in dental imaging.

Referring to FIG. 3, a computer environment 300 can interact with a user, for example, for viewing detected features (e.g., by interacting with the user-interface 206, shown in FIG. 2). Once a dental image is taken through the sensor 102 (shown in FIG. 1), the raw image data gets transferred to a computer system 302 included in the environment 300. From there, either in the raw image data or the post-processed image data (e.g., after the sensor's manufacturer's proprietary algorithms have processed the raw image data), gets exported or otherwise transferred (e.g. being exported to a memory associated with an Image Retriever 304 that is executed by the computer system 302. In one implementation, the image retriever 304 is a desktop client which de-identifies the dental image data by deleting or substituting with a non-identifiable replacement all personal health information, e.g. name, date of birth etc. and retains as associated dental image information only HIPAA compliant data of the subject (e.g., patient), the image was taken such as the gender, age, x-ray manufacturer and model of the dental image. Furthermore, the image retriever 304 can check if a dental image is a valid image in terms of having a correct image format, is an image which can be processed by the algorithm, and other filtering rules can apply that the right meta-data etc. contained in the image. The image 306 together with its associated dental image information (e.g. age, gender, x-ray modality, sensor, model, other meta-data, etc.), gets transferred over one of more networks (e.g., the internet 308) to a feature detector 310. To provide the functionality of detecting features, the feature detector 310 may use various machine learning techniques such as deep learning techniques to improve the identification processes through training the system (e.g., expose multilayer neural networks to training data, feedback, etc.). Through such machine learning techniques, the feature detector 310 uses artificial intelligence to automatically learn and improve from experience without being explicitly programmed. Once trained (e.g., from x-ray images with and without identified detected features (also called annotations)), one or more images, representation of images, etc. can be input into the feature detector 310 to yield an output. The machine learning may or may not be stored and retrieved at a storage device 316. In this example, access to an identifier 314 is provide through a computer system 312 (e.g., a server) located at the feature detector 310. Further, by returning information about the output (e.g., feedback), the machine learning technique being used by the identifier 314 can use the output as additional training information. Other training data can also be provided for further training. By using increased amounts of training data (e.g., dental images with and without detected features), feedback data (e.g., data representing user confirmation, correction or addition of identified detected features), etc., the accuracy of the system can be improved (e.g., to predict image features). In this illustrated example, the identifier 314 assigns a probability (e.g. numerical value ranging from 0 to 1, where a larger value is associated with greater confidence) that a pathology exists to each pixel in the dental image, which can be post-processed into various forms (e.g. see FIG. 1). An output is provided that represents a set of confidence scores for presence of detected image features (e.g., carious lesions and periapical lucencies), and a conditional probability map encoding the location of any detected image feature. In one arrangement, an augmented image 318 consisting of the original image, 306, the pixel-wise probability of a detected feature and a graphical representation, e.g., a bounding box, of the detected feature. This augmented image gets transferred back from the feature detector 310 to the computer system 302 where the image or portion of the image can be either displayed in a regular dental image viewer, the user-interface 206, other software user-interfaces, etc. The entire dental image system, consisting of the retriever 304 and the feature detector 310, can be either as described above both offline "on premise" on the computer system 302 and a connected network, such as the internet 308, or otherwise, completely offline on the computer system 302 or entirely in the cloud, meaning the internet 308.

Figure 4:
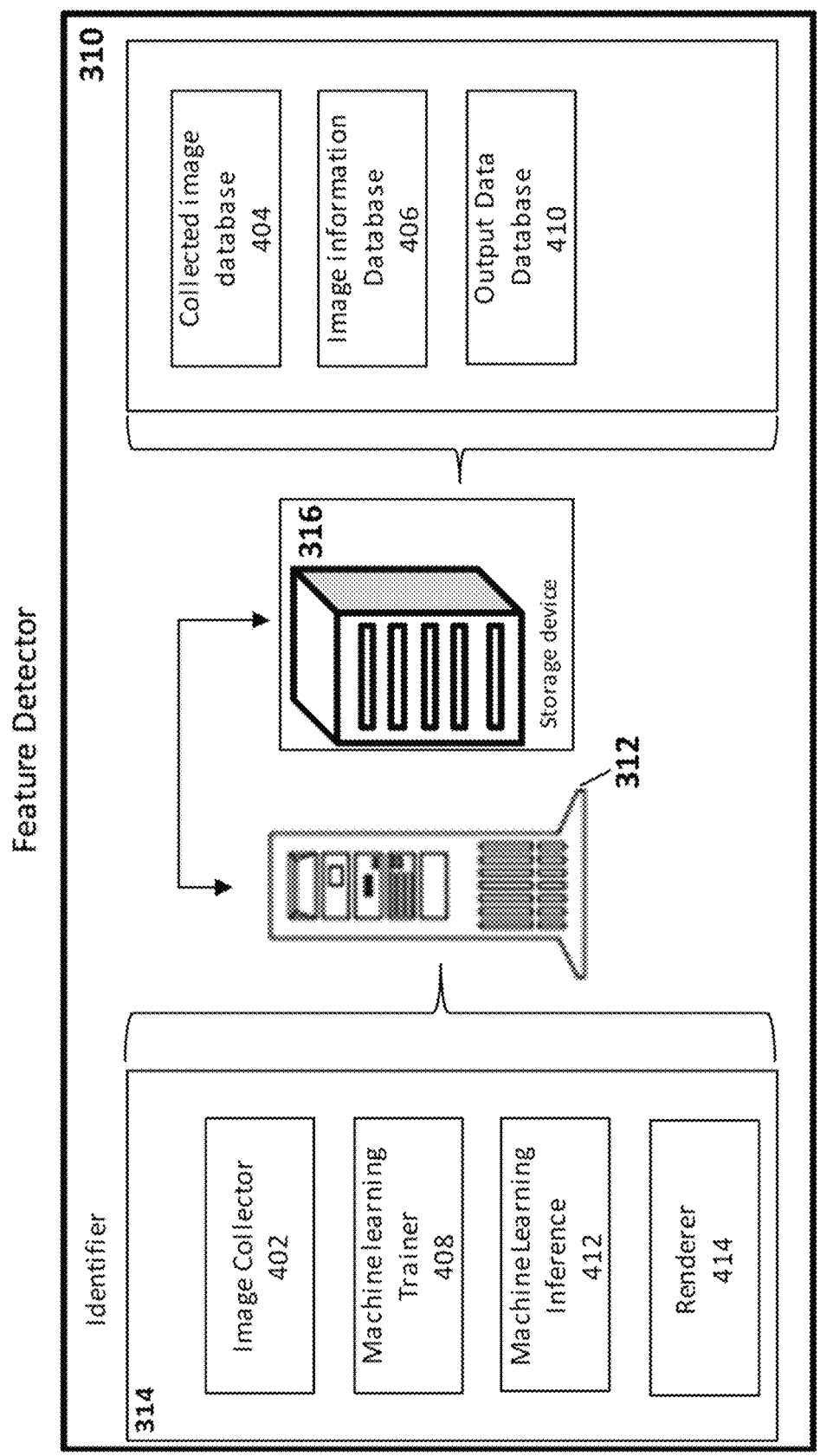
FIG. 4 a block diagram of the feature detector which manages and provides the detection of features in dental imaging.

Referring to FIG. 4, one or more techniques may be implemented to identify detected features in the dental images by executing operation on a computing device (e.g., the computing system 312). For such techniques, information may be used from one or more data sources. For example, a large data set from many dental practices, hospitals or other institutions who obtain dental images, might be collected in a collected image database 404. The identifier 314 is executed by the computer system 312 (e.g., one or more servers), presents at the feature detector 310 (also shown in FIG. 3). In this exemplary arrangement, the identifier 314 includes an image collector 402, which is able to collect images from the collected image database 404 and the image information database 406 which has associated dental image information data stored such as age, gender, and other image information which may or may not be frequently accessed and used for the identifier 314, regulatory or computational reasons both of which are hosted in the storage device 316. In this arrangement, such image data may be collected by an image collector 402 and stored (e.g., in a collected image database 404) on a storage device 316 for later retrieval. In some arrangements, information associated with images, associated dental image information (e.g., pixel-wise information of the area of the detected features which was collected by using the annotator tool, information about the subject—a patient, the image was taken from, image attributes such as manufacturers, model, lighting time, etc.) may be provided and stored in an image information database 406. Retrieving the image data (stored in database 404) and/or image information (stored in the database 406), a machine learning trainer 408 is provided the data to train a machine learning inference 412 (Going forward, a "machine learning system" is defined to consist of both the machine learning trainer 408 and the machine learning inference 412). Various type of data may be used for training the system; for example, images (e.g., millions of images) can be used by the trainer 408. For example, pristine images of dental images (e.g., portions of intra-oral bitewing or intra-oral periapical images), distorted images of dental images (e.g., synthetically altered versions), real-world images of dental intraoral cameras (e.g., images captured by individuals in real-world conditions that include one or more colored pictures of the teeth and gum inside the patient's mouth) may be used to train the machine learning inference 412. For some images of dental x-ray images (e.g., images of pristine full mouth series (i.e. a complete set of intraoral X-rays taken of a patients' teeth and adjacent hard tissue (often consisting of four bitewings, eight posterior periapicals, six anterior periapicals), synthetically altered versions of the same, etc.)), information that identifies each included dental image feature (e.g., labels) may be provided for training. Alternatively, for some images (e.g., captured under real-world conditions), identifying information (of included dental image features) may be absent. The trainer 408 can access the image collector data and use image collector data for training a machine learning model and store it at the output data base 410. Once trained, the machine learning inference 412 may be provided with input data such as one or more images to identify the dental features to detect or if the image quality is too low is present in the images. For example, after being trained using pristine, distorted, and real-world images of to be detected image features, images containing unidentified image features and captured under real-world conditions may be input for predicting the contained to be detected dental features (as illustrated in FIG. 2). The identifier 314 may output data that represents the predicted dental features or any other image features (e.g. too low of an image quality or the absence of such dental image features) determined through an analysis of the input image. The image information database 406 has corresponding information for the images in the collected image database 404 saved. This information includes, information48271—of the subject (e.g., patient) from whom the x-ray was taken, e.g., age and gender of the individual, the imaging device information, e.g., the type of imaging device (x-ray, CT, etc.), the area/type of image (bitewing or periapical dental image), the hardware model and version and other settings of the imaging device when the image was taken (e.g. all standardized DICOM tags) and the annotations. These annotations may or may not be generated by the data gathering, annotation and educational system as described in FIG. 9. The images from the collected image database can be presented to annotators (e.g. dentists, radiologists, other experts or non-experts) to annotate or mark the region where a feature of interest (e.g. carious lesion which the identifier should be capable of identifying) is to be found. The annotator can mark these regions either using a drawing a bounding box close around the feature of interest, by setting a point into the center of the feature of interest or by drawing an outline around the feature of interest. All these inputs are saved in the image information database 406 and can serve the trainer as training material. In one arrangement, each image does not only get an annotation from one individual but several individuals, e.g. three independent annotators, who annotate the same image. All annotations are typically saved in the image information database and a software module in the image collector 402 can automatically combine the multiple annotator annotations to generate a high-quality annotation. For example, the multiple annotator annotations can be combined in a majority voting system (if the two annotators agree on an annotation, the annotations overlap with each other for at least 1 pixel or have a certain value of "Intersection over Union", or a weighted union of all annotation by weighting more to the intersected regions) to define a higher quality annotation (e.g. 2 of 3 annotators agree on an annotation, it can be considered to be very likely a correct annotation, meaning an actual feature of interest). This system can be implemented in various ways such as having two annotators annotate images and add to data gathering system and then a third annotator serves as a referee and either agree or disagree with these annotations, and improve the quality of the annotations. By improving the annotations in such a way, the machine learning trainer can gather a much higher quality of annotations. For example, a single value can be output representing existence or absence of a feature in the entire image. In other arrangements, however, the output may be a vector or a matrix, which include a considerable number of elements (e.g., 1,000,000 elements), one for each pixel, each carious lesion, etc. A common output matrix can be a heatmap that has the same size as the input image (i.e., if image is in the size of 1440 by 1920 pixel, the matrix will have 1440 rows and 1920 columns) whose elements have a one-to-one correspondence to the pixels on the input dental image. Various types of data may be provided by each element to reflect how each individual pixel of input image is related to the to-be-detected feature, e.g. carious lesion (a cavity). For example, each element of the matrix may include a floating-point number that represents a level of confidence in detecting the feature, e.g. a carious lesion. In some arrangements, the sum of these element-wise quantities represent a predefined amount (e.g., a value of one) to assist comparing confidence levels and determining which dental image features, e.g. carious lesions, are closer matches. In this example, the output matrix (e.g., with 1440 by 1920 elements) from the machine learning inference 412 is stored in an output data database 410. A renderer 414 determines whether a detected image feature (e.g. carious lesion) are present based on the value of the confidence score and, for any lesion present, generates the coordinates of the lesion bounding box. The results determined by the renderer 414 (e.g., a list of pixel-coordinates of the detected feature and its rendered bounding box) can be stored on the storage device 316 (e.g., in an output data database 410) for later retrieval and use. For example, the input images (captured under real-world conditions) and correspondingly identified be further used to train the machine learning trainer 408 or other artificial intelligence based systems. The renderer 414 is using this heatmap and creates an image containing the original radiograph with bounding boxes for any detected feature, the type of detected feature (e.g. carious lesion or periapical radiolucency), and a summary statement of the number and type of detected features, and a message stating that the image was analyzed by the software (with link to instructions/labeling). The renderer 414 can transfer the augmented image 318 (or initiate the transfer) either back to the local computer environment 302 or visualize the image over an internet-based software client.

Figure 5:
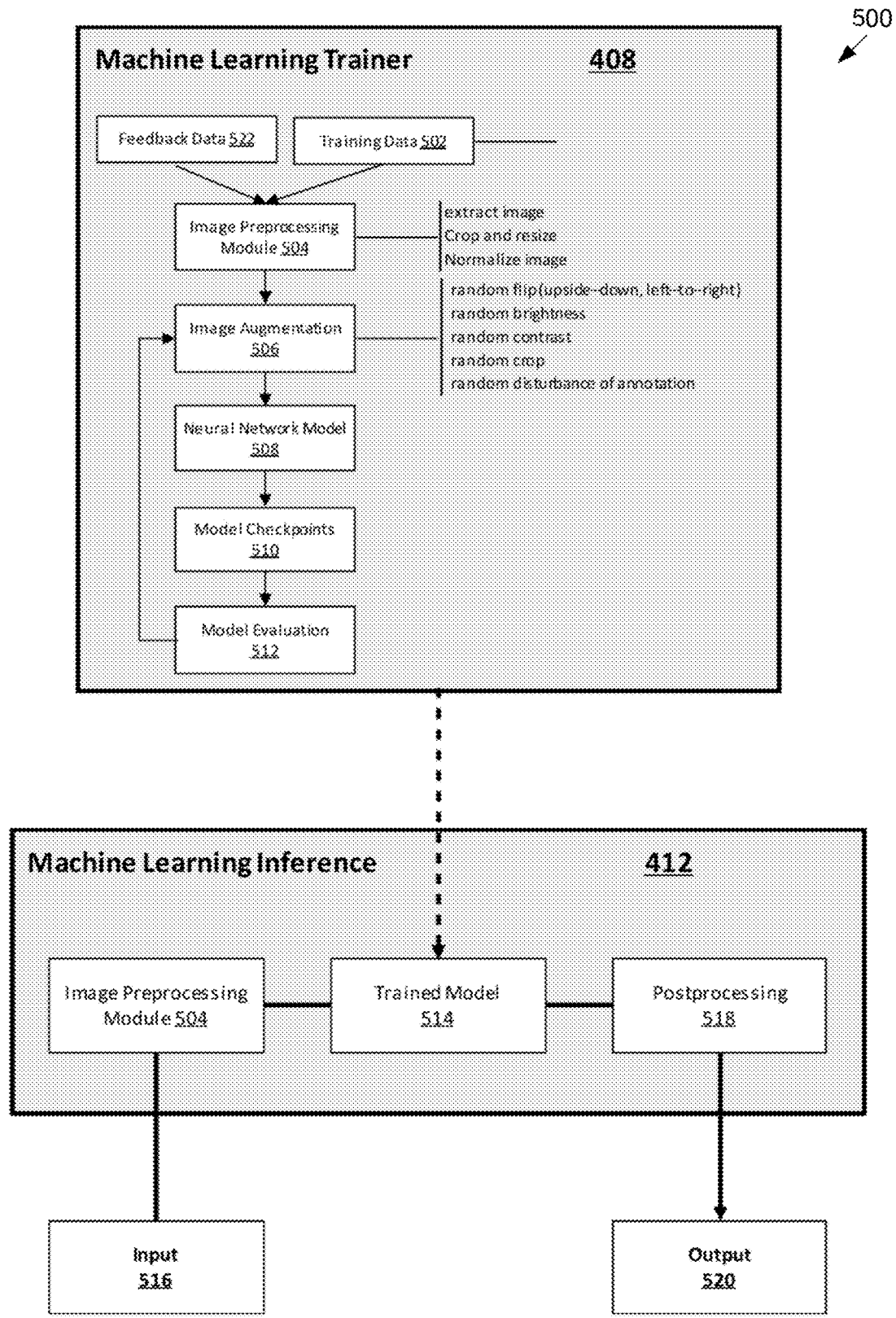
FIG. 5 illustrates the operations for training and inferencing the system for detecting features.

Referring to FIG. 5, a block diagram 500 is presented that provides a graphical representation of the functionality of the machine learning inference 412 and machine learning trainer 408 (shown also in FIG. 4). Prior to using the machine learning inference 412 to process an input 516 (e.g., a dental image and associated information, e.g., subject age, subject gender, sensor information) to produce an output 520 (e.g., a heat map, which is a matrix of same size as the input image whose elements represent the level of confidence of the corresponding pixel in the dental image as the potential detected feature, or a binary mask resulted from thresholding on the aforementioned heatmap, a bounding box localizing the detected feature in the dental image along with a level of confidence for that bounding box, etc.), the learning system needs to be trained. The machine learning trainer 408 includes several components. Various types of training data 502 may be used to prepare the machine learning trainer 408 to identify image features of interest to an end user. For example, dental images in pristine conditions, the corresponding annotations (bounding box for each feature which should be detected by the algorithm), and metadata describing some information about the image. This data can be in various formats, including but not limited to image formats, e.g., PNG TIFF, EXTIFF, databases, and DICOM file. In some instances, images may be used multiple times for system training to provide the dental image features and associated image information in one or more other forms. From this data, images are extracted by Image Processing Module 504 and resized and cropped to the appropriate shapes. The intensities of the images are normalized to correct for acquisition variability of scanners and detectors. These images are then further processed by Image Augmentation 506 to include random changes in the images in order to increase variability of the images, prevent the model to overfit to these images, and finally make the model more robust. These random changes include randomly flipping the image upside-down or left-to-right, randomly change the overall brightness or contrast of the image, randomly crop the image into smaller size, and randomly make small changes to the annotation. Next, these processed images are fed to a Neural Network Model 508, which iteratively learns the values for the parameters of the model to predict the annotation given each image. These values, called weights, and are saved along with the model architecture at Model Checkpoints 510. Finally, at Model Evaluation 512, the neural network model 508 (consisting of architecture and weights) are evaluated on unseen and separate data from the Training Data 502, and metrics of success is being reported. This procedure from Image Augmentation 506 to Model Evaluation 512 is repeated until the threshold for metrics of success are met. The model that meet these criteria is considered as a Trained Model 514 and is used in the production and for Machine Learning Inference 412. In some arrangements feedback data 522, which can come from various sources e.g. detected features from a previous machine learning model which output has been clinically validated or validated by another annotator, dental clinician or user, can also be provided to the machine learning trainer to further improve training. The training data 502 may also include segments of one training image. For example, one image may be segmented into five separate images that focus on different areas of the original image. For prediction operations, a prediction result (e.g., a binary mask, a heatmap or a bounding box along with its confidence level) can be attained for each segment and an overall result determined (e.g., by averaging the individual results) to improve prediction accuracy. One image may be cropped from the original image to focus upon the upper left quadrant of the original image while three other segments may be cropped to focus on the upper right, lower left, and lower right portions of the original image, respectively. A fifth image segment may be producing by cropping the original image to focus upon the central portion of the original image. Various sizes and shapes may be used to create these segments; for example, the original image may be of a particular size (e.g., 512 by 512 pixels, 1440 by 1920 pixels, etc.) while the segments are of lesser size (e.g., 256 by 256 pixels). In one arrangement, which is called active learning, after initial training with the first set of annotated dental images (e.g., 5,000 dental images), for each new dental image, which has not been annotated (each remaining of the 10,000 dental images for instance), operations are executed (by the identifier 314) to determine the most valuable images for further annotation and training.

In production phase, the Input 516 is typically an image (or a set of images) without any annotation. This image is usually processed with the same Image Preprocessing Module 504 that is used in Machine Learning Trainer 408. Then, without any further processing, the image is fed to the Trained Model 514 and the model predict the target output (e.g., a bounding box, a heatmap, or a binary mask) for any present detected feature. These intermediate outputs are put together and superimposed on the original input image in Postprocessing 518 and results in the Output 520 that can be rendered on the users' workstation.

To train the machine learning trainer 408 and implement algorithms into the machine learning inference 412, one or more machine learning techniques may be employed. For example, supervised learning techniques may be implemented in which training is based on a desired output that is known for an input. Supervised learning can be considered an attempt to learn a nonlinear function that maps inputs to outputs and then estimate outputs for previously unseen inputs (a newly introduced input). Depending on the desired output, these supervised learning methods learn different nonlinear functions and perform different tasks. The output can be just a text or alarm that signal the presence or absence of a lesion or any other feature of interest like number of teeth. This task is being done by classification methods, but if the output is a continuous value like the size of a cavity, regression methods are being used. On the other hand, the output can be a visual feature, like the delineation of a tooth or a lesion or just a box that includes that tooth or lesion. Using exact delineation of a feature of interest as the output, we can employ segmentation algorithms to perform the supervised learning task. When boxes that are superimposed on the input images, called bounding boxes, are used as the desired output, the object detection algorithms are employed. Unsupervised learning techniques may also be employed in which training is provided from known inputs but unknown outputs. Dimensionality reduction methods are example such techniques that tries to find patterns in the data and can create a more compact representation of the image. This compact representation then can be correlated to certain features of interest. Reinforcement learning techniques may also be used in which the system can be considered as learning from consequences of actions taken (e.g., inputs values are known). This can be mainly used for dental treatment planning, like orthodontics treatment, to learning the optimal treatment strategy. In some arrangements, the implemented technique may employ two or more of these methodologies. In some arrangements, neural network techniques may be implemented using the data representing the images (e.g., a matrix of numerical values that represent visual elements such as pixels of an image, etc.) to invoke training algorithms for automatically learning the images and related information. Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to training data. By using the image data (e.g., attribute vectors), a function may be defined that quantifies error (e.g., a squared error function used in regression techniques). By minimizing error, a neural network may be developed that is capable of determining attributes for an input image. One or more techniques may be employed by the machine learning system (the machine learning trainer 408 and machine learning system 412), for example, backpropagation techniques can be used to calculate the error contribution of each neuron after a batch of images is processed. Stochastic gradient descent, also known as incremental gradient descent, can be used by the machine learning system as a stochastic approximation of the gradient descent optimization and iterative method to minimize a loss function. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implements to reduce its effects. Other types of artificial intelligence techniques may be employed about the identifier 314 (shown in FIG. 3 and FIG. 4). For example, the machine learning inference 412 and machine learning trainer 408 can use neural networks such as a generative adversarial networks (GANs) in its machine learning architecture (e.g., an unsupervised machine learning architecture). In general, a GAN includes a generator neural network, a different specific x implementation kind of the Image Augmentation 506, that generates data (e.g., different versions of the same image by flips, inversions, mirroring etc.) that is evaluated by a discriminator neural network, a specific type of the Neural Network Model 508, for authenticity (e.g., to identify the dental images). In other words, the discriminator neural network, a specific type of the Neural Network Model 508, attempts to identify the detected feature included in the augmented image (e.g., a distorted version of a dental image) provided by the generator, a different specific implementation of the Image Augmentation 506. Various implementations for GAN generators and discriminators may be used; for example, the discriminator neural network, a specific type of the Neural Network Model 508, can use a convolutional neural network that categorizes input images with a binomial classifier that labels the images as genuine or not. The generator neural network, a different specific implementation of the Image Augmentation 506, can use an inverse convolutional (or deconvolutional) neural network that takes a vector of random noise and upsamples the vector data to an image to augment the image.

Other forms of artificial intelligence techniques may be used by the machine learning trainer 408 and machine learning inference 412. For example, to process information (e.g., images, image representations, etc.) to identify detected features of the x-ray image, such as potential cavities and periapical radiolucencies, the architecture may employ decision tree learning that uses one or more decision trees (as a predictive model) to progress from observations about an item (represented in the branches) to conclusions about the item's target (represented in the leaves). In some arrangements, random forests or random decision forests are used and can be considered as an ensemble learning method for classification, regression and other tasks. Such techniques generally operate by constructing a multitude of decision trees at training time and outputting the class that is the mode of the classes (classification) or mean prediction (regression) of the individual trees. Support vector machines (SVMs) can be used that are supervised learning models with associated learning algorithms that analyze data used for classification and regression analysis. Ensemble learning systems may also be used for detecting features in dental images in which multiple system members independently arrive at a result. The ensemble typically comprises not only algorithms with diverse architectures, but also algorithms trained on multiple independent data sets. In one arrangement, a convolutional neural network architecture can be used that is based on U-Net to perform image segmentation to identify detected features, e.g. radiolucent lesions and carious lesions on the dental x-ray images. This implementation of the network uses batch-normalization after each convolutional layer has a tunable depth. The network parameters (weights) are trained using the Jaccard Index metric as a loss function, where true positive, false positive and false negative counts are measured across all images in a batch/mini-batch. The algorithm assigns a probability (e.g. number ranging from 0 to 1, where a larger value is associated with greater confidence) that a pathology exists to each pixel in the x-ray image, which can be post-processed into various non-graphical or graphical forms (e.g. see 208). The algorithm is trained using data augmentation of the images and ground truth regions, for example one or more of rotations, scaling, random crops, translations, image flips, and elastic transformations; the amount of augmentation for each transformation is tuned to optimize performance of the algorithm on the available data. System members can be of the same type (e.g., each is a decision tree learning machine, etc.) or members can be of different types (e.g., one Deep CNN system, one SVM system, one decision tree system, etc.). Upon each system member determining a result, a majority vote among the system members is used (or other type of voting technique) to determine an overall prediction result. In some arrangements, one or more knowledge-based systems such as an expert system may be employed. In general, such expert systems are designed by solving relatively complex problems by using reasoning techniques that may employ conditional statements (e.g., if-then rules). In some arrangements such expert systems may use multiple systems such as a two sub-system design, in which one system component stores structured and/or unstructured information (e.g., a knowledge base) and a second system component applies rules, etc. to the stored information (e.g., an inference engine) to determine results of interest (e.g., select images likely to be presented).

System variations may also include different hardware implementations and the different uses of the system hardware. For example, multiple instances of the machine learning system identifier 314 may be executed through the use of a single graphical processing unit (GPU). In such an implementation, multiple system clients (each operating with one machine learning system) may be served by a single GPU. In other arrangements, multiple GPU's may be used. Similarly, under some conditions, a single instance of the machine learning system may be capable of serving multiple clients. Based upon changing conditions, multiple instances of a machine learning system may be employed to handle an increased workload from multiple clients. For example, environmental conditions (e.g., system throughput), client-based conditions (e.g., number of requests received per client), hardware conditions (e.g., GPU usage, memory use, etc.) can trigger multiple instances of the system to be employed, increase the number of GPU's being used, etc. Similar to taking steps to react to an increase in processing capability, adjustments can be made when less processing is needed. For example, the number of instances of a machine learning system being used may be decreased along with the number of GPU's needed to service the clients. Other types of processors may be used in place of the GPU's or in concert with them (e.g., combinations of different types of processors). For example, central processing units (CPU's), processors developed for machine learning use (e.g., an application-specific integrated circuit (ASIC) developed for machine learning and known as a tensor processing unit (TPU)), etc. may be employed. Similar to GPU's one or more models may be provided by these other types of processors, either independently or in concert with other processors.

Figure 6:
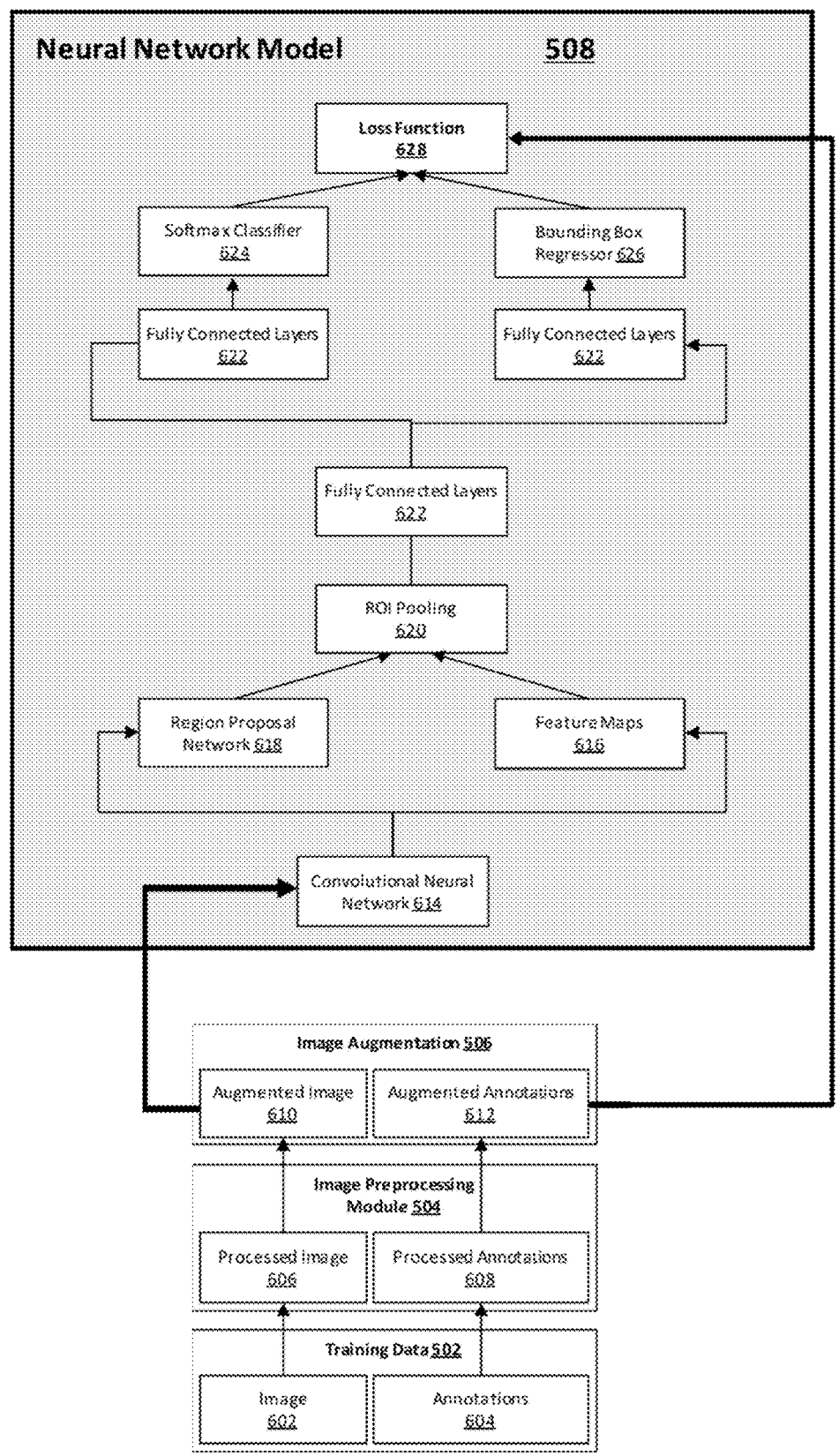
FIG. 6 illustrates an exemplary architecture of a neural network model.

FIG. 6 illustrates an exemplary meta-architecture for the Neural Network Model 508, according to various arrangements. This meta-architecture is for object detection with region proposal network. The Training Data 502 consists of Image 602 and Annotations 604 (meaning the pixel coordinate information of the to be detected features and, in an arrangement, additional dental image associated information such as image's subject information such as age, gender, etc. and other parameters of the image such as contrast, width, pixel-depth, etc.). Each of these components are separately processed and prepared by the Image Processing Module 504 to obtain Processed Image 606 and Processed Annotations 608, which are ready to be fed to the model. However, usually we further process and augment them (e.g., only during training) to obtain Augmented Image 610 and Augmented Annotations 612. These are usually the two inputs to the (deep) neural network model 508. Augmented Image 610 go through Convolutional Neural Network 614, which consists of many convolutional layers (e.g. 101 layers). The output of this network is bifurcated to be used in two parallel tasks. One is extracting the learned features and create Feature Maps 616 and the other is used by a Region Proposal Network 618 to propose bounding boxes with different shape and size associated to each target class. Then these bounding boxes are merged with the feature maps through region of interest (ROI) Pooling 620, and create region of interests (ROI's), which are potential candidates for detection. These ROI's go through Fully Connected Layers 622, which are social types of neural network layers where components are densely connected to the components of previous layer. Next, this output is bifurcated with independent Fully Connected Layers 622 for classification of type of the detection, using a Softmax Classifier 624, and tightening the bounding boxes using a Bounding-box Regressor 626. The model is trained by combining the output of the Softimax Classifier 624 and the Bounding Box Regressor 626 to build a Loss Function 628 and minimize the value of this Loss Function 628 via one or more optimization methods, such as stochastic gradient decent. In other instances, other meta-architectures can be employed that may or may not rely on region proposal. These meta-architectures include but not limited to Single Shot Multi Box Detector, YOLO9000, YOLOv2, YOLOv3, Feature Pyramid Networks, RetinaNet.

Figure 7:
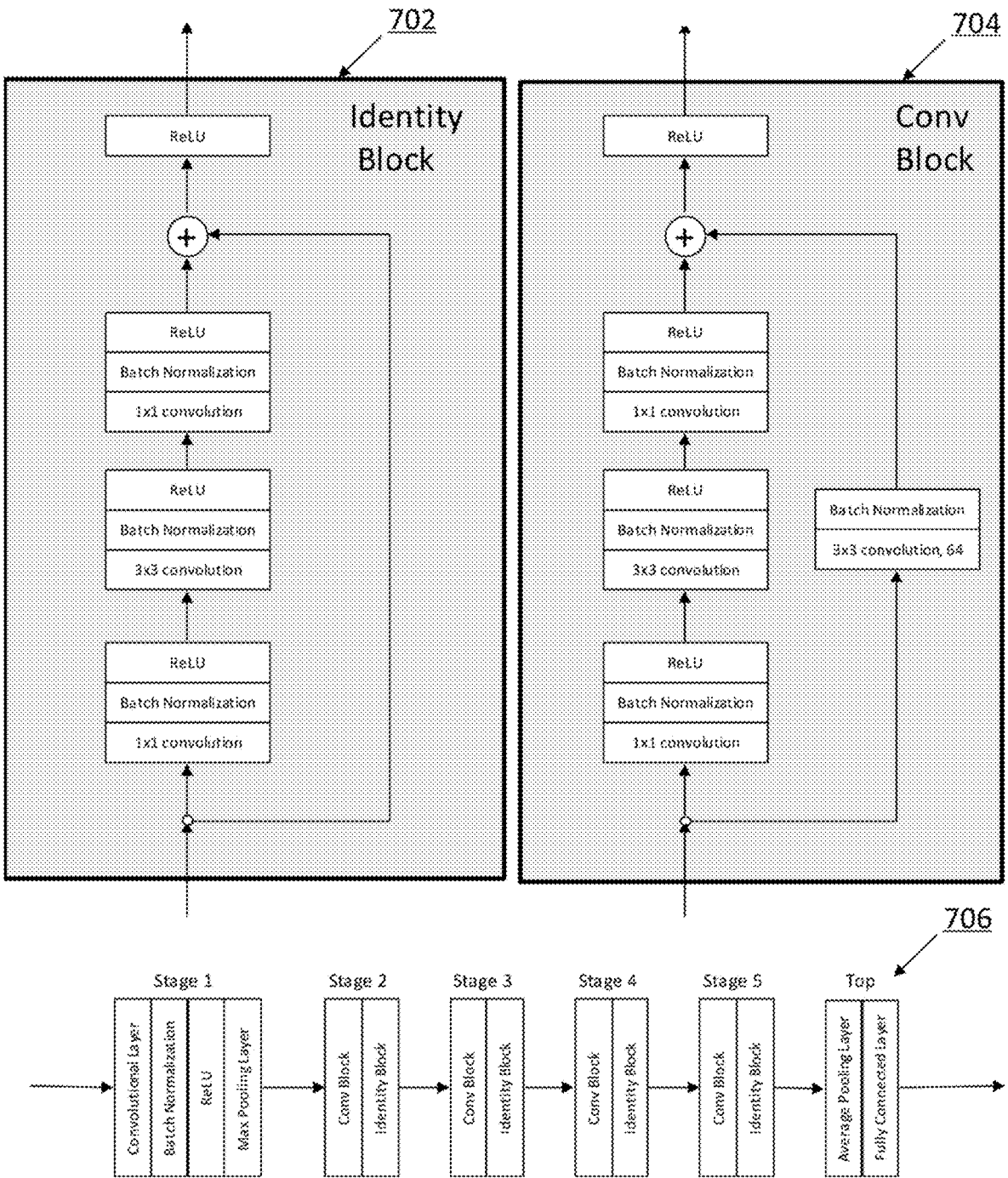
FIG. 7 illustrates an exemplary network architecture for a convolutional neural network.

FIG. 7 illustrates an exemplary network architecture for the Convolutional Neural Network 614, according to various arrangements. In this example, two special neural network's blocks are employed: an Identity Block 702 and a Cony Block 704. These blocks are used in a sequence to build a deep neural network architecture, referred to as ResNet Architecture 706. There are various ways to build a deep neural network architecture, either putting together these building blocks to create a customized network or use pre-existing architectures like AlexNet, VGQ DenseNet, InceptionV3, Xception, MobileNet, NASNet, etc. The number of parameters in these architectures can vary from few hundreds to hundreds of millions of parameters.

Figure 8:
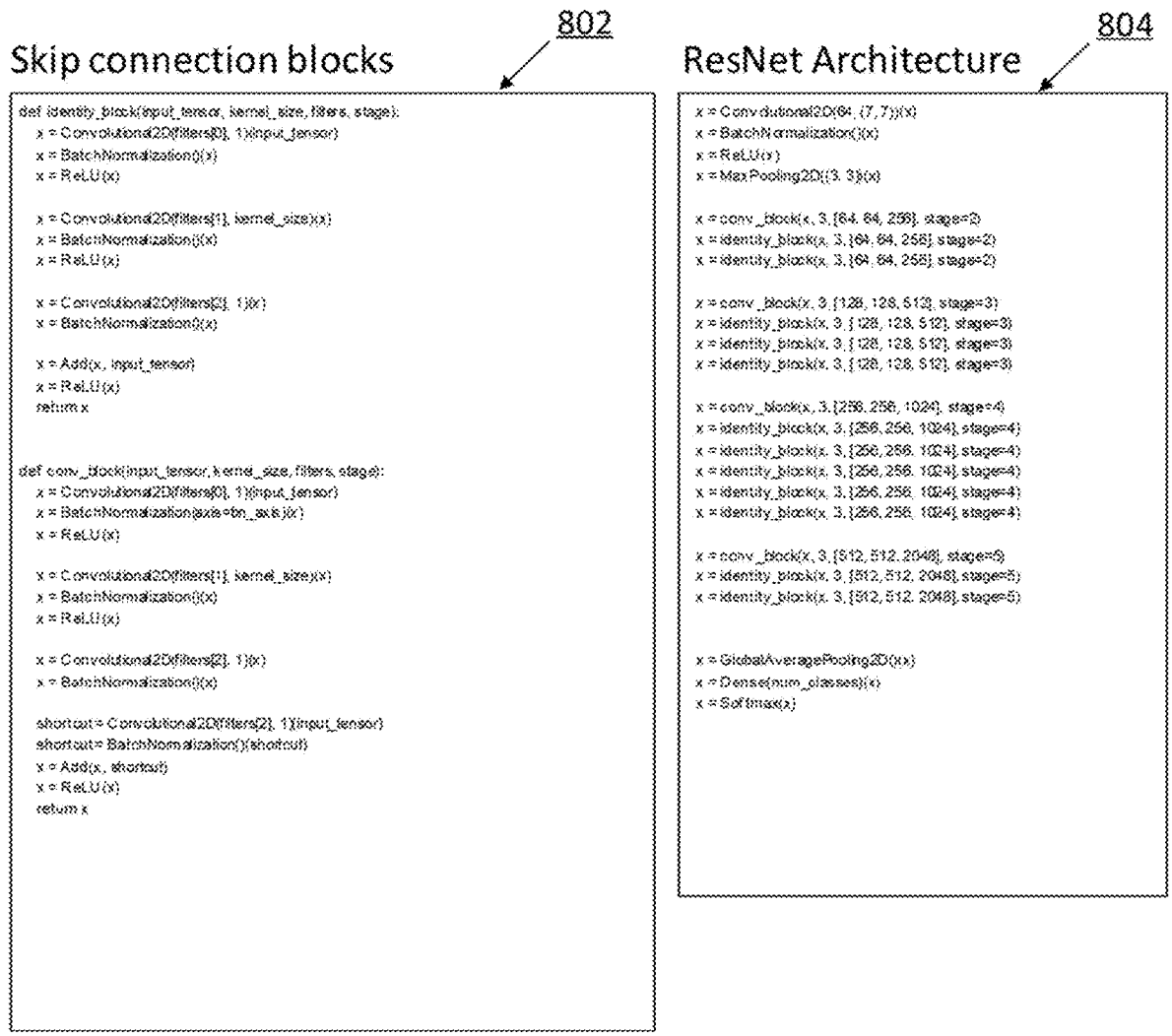
FIG. 8 shows the instructions for a convolutional neural network architecture.

FIG. 8 shows the instructions to build the convolutional neural network architecture. Section 802 shows the detailed instruction of skip connection building blocks (Identity Block 702 and Cony Block 704) where the input bifurcate goes through a sequence of convolutional and batch normalization layer with ReLU activations on one branch and just one convolution and batch normalization (Cony Block 704) or no operation (Identity Block 702) in other branch. These branches are merged at the end of the block by adding them together. Section 804 includes instructions for ResNet Architecture 706, which uses the aforementioned blocks along with convolutional, batch-normalization, max pooling, and average pooling later to build a convolutional neural network model.

Figure 9:
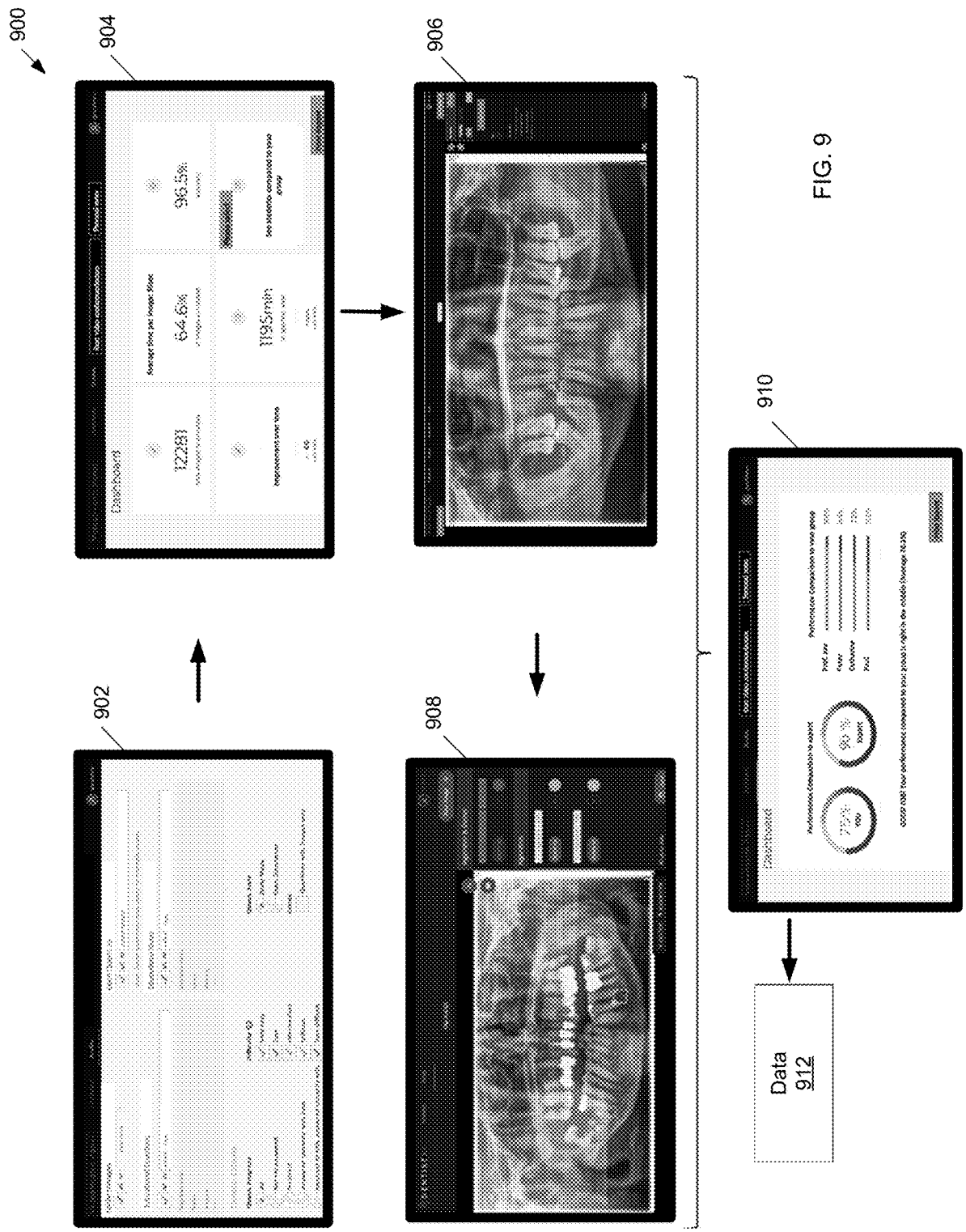
FIG. 9 illustrates a data gathering, annotation and educational system.

Referring to FIG. 9, a flowchart of screenshots presents a data gathering, annotation and educational system. The flowchart represents the gathering of various types of data from the user of the system, the subject of the system (e.g. dental images) to collect training data for the operations executed at the Feature Detector 310, locally at the computer system 302 or in the internet, etc. as described with respect to FIG. 1-7, to train dental professionals (e.g. students, dentists, etc.) and to conduct research studies. In an administrative interface 902, an administrator (e.g. professor, manager etc.) can select images, types of detected features he would like the annotator/user to annotate/mark, questions he might want to ask and other characteristics of the tasks (e.g. the type of imaging). He can then send out the task to the annotator/user, (e.g. dentists, student, any other human being or computer), who can see an overview of his performance on an annotator/user-dashboard 904. In this dashboard the annotator/user can access "Annotations tasks", "Training/learning tasks", and "quiz tasks". Once selected e.g. the annotation task, the user is transferred to the annotator tool 906. This module has x-ray viewer capabilities (e.g., inversion, change of contrast, etc.) and can be used to diagnose the dental image and input an "annotation". For example, the user can provide a e.g. bounding box, or an outline around the image feature that is detected by the identifier 314 (shown in FIG. 3). In an arrangement of the system, after annotating the image, the next module can be the comparison interface 908. This interface 908 compares the annotation of the user, with either the algorithmic analysis of such image or any other annotation of another user or a group of other users. The interface 908 automatically detects if there is an agreement between the user and this algorithmic/other user annotation (e.g. by an overlap of minimum one pixel). If there is no overlap, the user can decide if he agrees with the algorithmic/other user annotation or not. All this input data (e.g. the pixel-wise location of the annotation of the user, the location of the algorithmic/other user annotation, the agreement or disagreement between the two, the use of contrast, inversion, time spend on the dental image etc.) gets saves in the backend. One or more comparison techniques automatically calculates performance metrics for the user to have an expert. It computes the false positive, true positive and true negative value of the user's annotations based on some "ground-truth" standard which has been previously defined. This ground-truth standard can either be based on an expert (e.g. professor) who annotated the images previously, based on clinical studies which assessed the patients of the dental imaging, medical records, a combination of many people annotations or any other mean. Comparing the user's annotations against this ground-truth, the other user's annotations and the algorithmic annotation (output), allows the system to compute a variety of performance metrices such as how "accurate" in terms of specificity and sensitivity the user is compared to other users, other experts or compared to the algorithm. This data 912 can be output and used by the dental software system in a variety of ways. In an arrangement, not all images that are annotated need to have a pre-defined ground-truth. Furthermore, by accumulating several user's annotation for the same image, these annotations can be groups using specific clustering algorithms, calculating agreement rates and providing us with better training data for the identifier 314. At the same time, it allows medical professionals (e.g. dental students, dentists, radiologists) to close the often-missing feedback loop in medicine. Often you do not know if an assessment was actually correct or not as you do not see the patient again or the diagnosis/treatment does not allow to observe the counter-factual. This system is an interactive training system to better learn to diagnose dental and other types of medical imaging and at the same time allows to collect valuable data to train artificial intelligence software.

Figure 10:
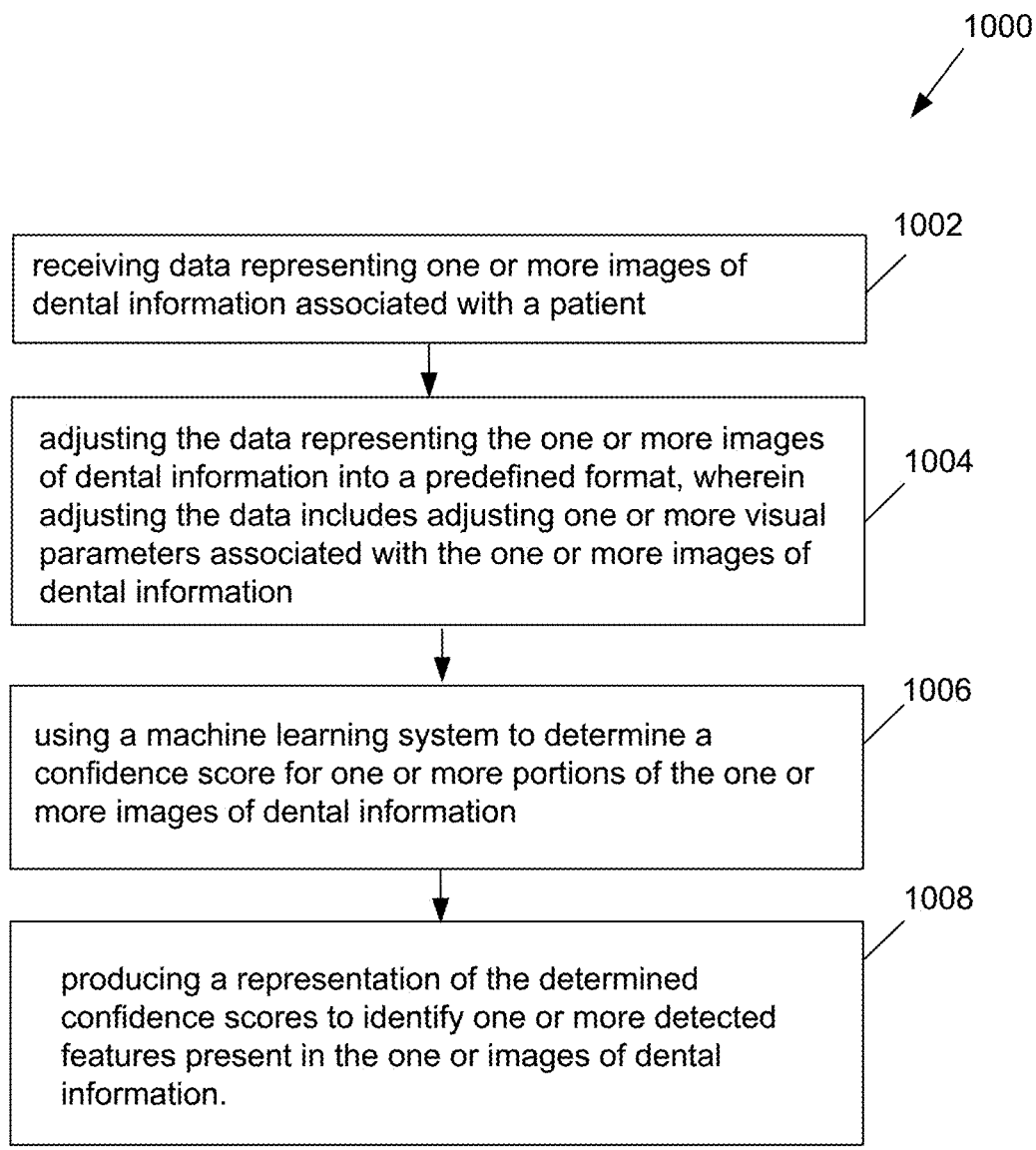
FIG. 10 illustrates a flow chart of operations executed by an identifier.

Referring to FIG. 10, a flowchart 1000 represents operations of the identifier 314 (shown in FIG. 3). Operations of the identifier 314 are typically executed by a single computing device (e.g., the computer system 312); however, operations of the identifier may be executed by multiple computing devices. Along with being executed at a single site, execution of operations may be distributed among two or more locations.

Operations of the identifier include receiving 1002 data representing one or more images of dental information associated with a patient. For example, one or multiple radiographic images may be received that contain dental information about a patient or multiple patients (e.g., jaw and teeth images). Operations also include adjusting 1004 the data representing the one or more images of dental information into a predefined format. For example, raw imagery may be processed to being represented in a DICOM format or other time of image format. Adjusting the data includes adjusting one or more visual parameters associated with the one or more images of dental information. For example, imagery, information associated with the images, etc. may be filtered or processed in other manners. Operations also include using 1006 a machine learning system to determine a confidence score for one or more portions of the one or more images of dental information. For example, a confidence score (e.g., having a numerical value from 0 to 1) can be assigned to each pixel associated with a dental image that reflects the presence of a feature (e.g., e.g., carious lesions and periapical lucencies). Operations also include producing 1008 a representation of the determined confidence scores to identify one or more detected features present in the one or more images of dental information. For example, graphical representation (e.g., colored bounding boxes) may be presented on a graphical interface to represent the certainty score and alert the viewer to the detected features.

Figure 11:
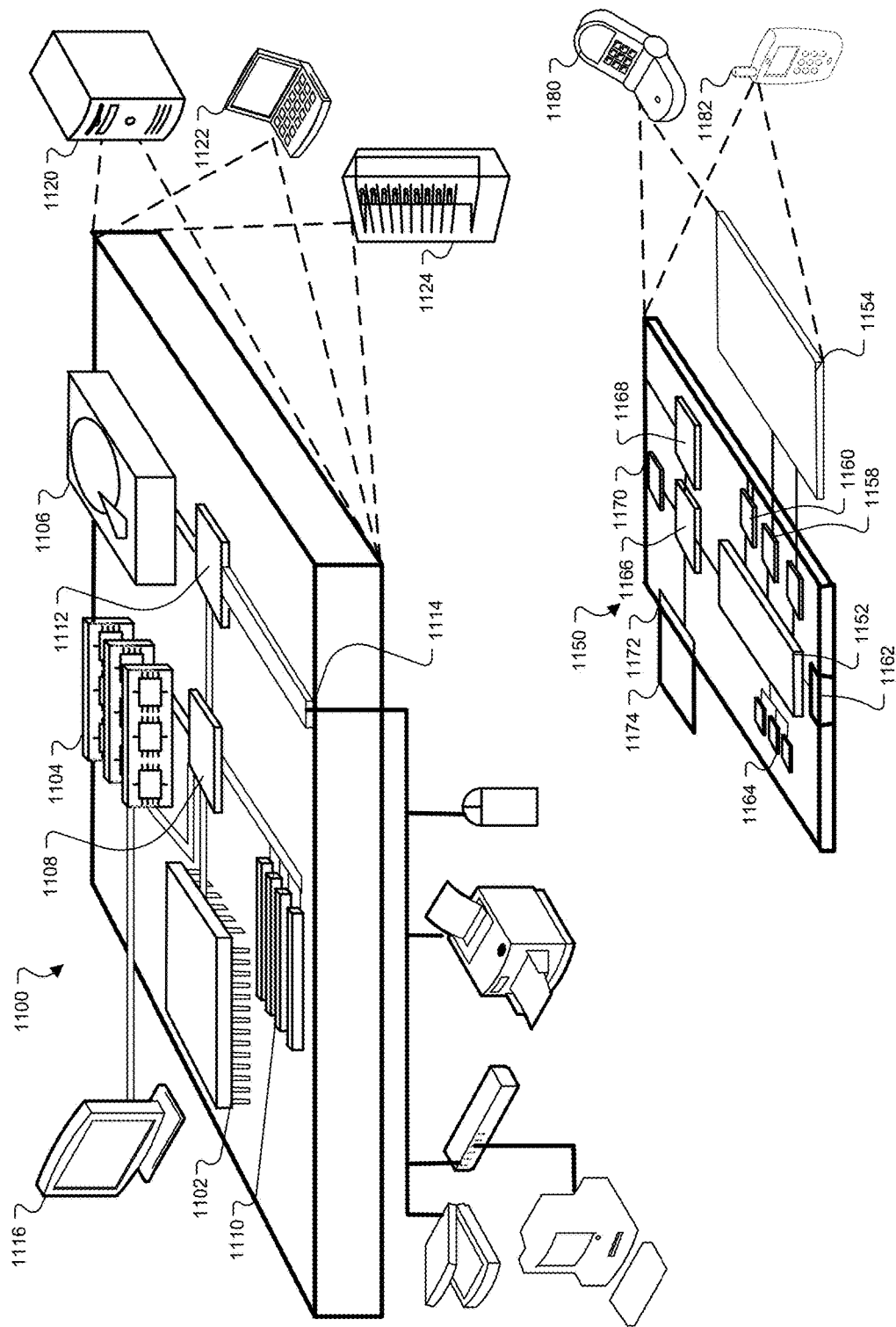
FIG. 11 illustrates an example of a computing device and a mobile computing device that can be used to implement the techniques described here.

FIG. 11 shows an example of example computer device 1100 and example mobile computer device 1150, which can be used to implement the techniques described herein. For example, a portion or all of the operations of the identifier 314 (shown in FIG. 3) may be executed by the computer device 1100 and/or the mobile computer device 1150. Computing device 1100 is intended to represent various forms of digital computers, including, e.g., laptops, desktops, workstations, personal digital assistants, servers, blade servers, mainframes, and other appropriate computers. Computing device 1150 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 1100 includes processor 1102, memory 1104, storage device 1106, high-speed interface 1108 connecting to memory 1104 and high-speed expansion ports 1110, and low speed interface 1112 connecting to low speed bus 1114 and storage device 1106. Each of components 1102, 1104, 1106, 1108, 1110, and 1112, are interconnected using various busses, and can be mounted on a common motherboard or in other manners as appropriate. Processor 1102 can process instructions for execution within computing device 1100, including instructions stored in memory 1104 or on storage device 1106 to display graphical data for a GUI on an external input/output device, including, e.g., display 1116 coupled to high speed interface 1108. In other implementations, multiple processors and/or multiple busses can be used, as appropriate, along with multiple memories and types of memory. Also, multiple computing devices 1100 can be connected, with each device providing portions of the necessary operations (e.g., as a server bank, a group of blade servers, or a multi-processor system).

Memory 1104 stores data within computing device 1100. In one implementation, memory 1104 is a volatile memory unit or units. In another implementation, memory 1104 is a non-volatile memory unit or units. Memory 1104 also can be another form of computer-readable medium (e.g., a magnetic or optical disk. Memory 1104 may be non-transitory.)

Storage device 1106 is capable of providing mass storage for computing device 1100. In one implementation, storage device 1106 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 1104, storage device 1106, memory on processor 1102, and the like.)

High-speed controller 1108 manages bandwidth-intensive operations for computing device 1100, while low speed controller 1112 manages lower bandwidth-intensive operations. Such allocation of functions is an example only. In one implementation, high-speed controller 1708 is coupled to memory 1104, display 1116 (e.g., through a graphics processor or accelerator), and to high-speed expansion ports 1110, which can accept various expansion cards (not shown). In the implementation, low-speed controller 1112 is coupled to storage device 1106 and low-speed expansion port 1114. The low-speed expansion port, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.)

Computing device 1100 can be implemented in a number of different forms, as shown in the figure. For example, it can be implemented as standard server 1120, or multiple times in a group of such servers. It also can be implemented as part of rack server system 1124. In addition or as an alternative, it can be implemented in a personal computer (e.g., laptop computer 1122.) In some examples, components from computing device 1100 can be combined with other components in a mobile device (not shown), e.g., device 1150. Each of such devices can contain one or more of computing device 1100, 1150, and an entire system can be made up of multiple computing devices 1100, 1150 communicating with each other.

Computing device 1150 includes processor 1152, memory 1164, an input/output device (e.g., display 1154, communication interface 1166, and transceiver 1168) among other components. Device 1150 also can be provided with a storage device, (e.g., a microdrive or other device) to provide additional storage. Each of components 1150, 1152, 1164, 1154, 1166, and 1168, are interconnected using various buses, and several of the components can be mounted on a common motherboard or in other manners as appropriate.

Processor 1152 can execute instructions within computing device 1150, including instructions stored in memory 1164. The processor can be implemented as a chipset of chips that include separate and multiple analog and digital processors. The processor can provide, for example, for coordination of the other components of device 1150, e.g., control of user interfaces, applications run by device 1150, and wireless communication by device 1150.

Processor 1152 can communicate with a user through control interface 1158 and display interface 1156 coupled to display 1154. Display 1154 can be, for example, a TFT LCD (Thin-Film-Transistor Liquid Crystal Display) or an OLED (Organic Light Emitting Diode) display, or other appropriate display technology. Display interface 1156 can comprise appropriate circuitry for driving display 1154 to present graphical and other data to a user. Control interface 1158 can receive commands from a user and convert them for submission to processor 1152. In addition, external interface 1162 can communicate with processor 1142, so as to enable near area communication of device 1150 with other devices. External interface 1162 can provide, for example, for wired communication in some implementations, or for wireless communication in other implementations, and multiple interfaces also can be used.

Memory 1164 stores data within computing device 1150. Memory 1164 can be implemented as one or more of a computer-readable medium or media, a volatile memory unit or units, or a non-volatile memory unit or units. Expansion memory 1174 also can be provided and connected to device 1150 through expansion interface 1172, which can include, for example, a SIMM (Single In Line Memory Module) card interface. Such expansion memory 1174 can provide extra storage space for device 1150, or also can store applications or other data for device 1150. Specifically, expansion memory 1174 can include instructions to carry out or supplement the processes described above, and can include secure data also. Thus, for example, expansion memory 1174 can be provided as a security module for device 1150, and can be programmed with instructions that permit secure use of device 1150. In addition, secure applications can be provided through the SIMM cards, along with additional data, (e.g., placing identifying data on the SIMM card in a non-hackable manner.)

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 1164, expansion memory 1174, and/or memory on processor 1152), which can be received, for example, over transceiver 1168 or external interface 1162.

Device 1150 can communicate wirelessly through communication interface 1166, which can include digital signal processing circuitry where necessary. Communication interface 1166 can provide for communications under various modes or protocols (e.g., GSM voice calls, SMS, EMS, or MMS messaging, CDMA, TDMA, PDC, WCDMA, CDMA2000, or GPRS, among others.) Such communication can occur, for example, through radio-frequency transceiver 1168. In addition, short-range communication can occur, e.g., using a Bluetooth®, WiFi, or other such transceiver (not shown). In addition, GPS (Global Positioning System) receiver module 1170 can provide additional navigation- and location-related wireless data to device 1150, which can be used as appropriate by applications running on device 1150. Sensors and modules such as cameras, microphones, compasses, accelerators (for orientation sensing), etc. may be included in the device.

Device 1150 also can communicate audibly using audio codec 1160, which can receive spoken data from a user and convert it to usable digital data. Audio codec 1160 can likewise generate audible sound for a user, (e.g., through a speaker in a handset of device 1150.) Such sound can include sound from voice telephone calls, can include recorded sound (e.g., voice messages, music files, and the like) and also can include sound generated by applications operating on device 1150.

Computing device 1150 can be implemented in a number of different forms, as shown in the figure. For example, it can be implemented as cellular telephone 1180. It also can be implemented as part of smartphone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A computing device implemented method comprising:
    receiving data representing one or more images of dental information associated with a patient, the one or more images containing one or more unidentified image features of the patient;
    adjusting the data representing the one or more images of dental information into a predefined format, wherein adjusting the data includes adjusting one or more visual parameters associated with the one or more images of dental information;
    using a machine learning system based on one or more neural networks to determine one or more confidence scores for the presence of at least one detectable feature,
    each of the one or more confidence scores corresponding to one or more distinct portions of the one or more images of dental information,
    the at least one detectable feature representing at least one or more diseases, one or more prior procedures performed upon the patient, or one or more anatomical structure characteristics, and
    the machine learning system being trained with dental imagery comprising one or more training images, wherein annotations of the one or more training images are provided by different annotators;
    producing a representation based on the determined one or more confidence scores, the representation comprising information about a presence or absence of the at least one detectable feature, and
a tooth number associated with the at least one detectable feature, if present, within the one or more images of dental information,
wherein the information in the produced representation is selectively presented based upon user input;
comparing the at least one detectable feature and patient data to represent a mapping and to represent a measure of a dental management system, and
generating a report comprising the at least one detectable feature.

2. The computing device implemented method of claim 1, further comprising: transferring the data representing the one or more images of dental information associated with the patient to one or more networked computing devices for statistical analysis.

3. The computing device implemented method of claim 1, wherein the machine learning system employs a convolution neural network.

4. The computing device implemented method of claim 1, wherein the at least one detectable feature includes a radiolucent lesion or an opaque lesion.

5. The computing device implemented method of claim 1, wherein the produced representation includes a graphical representation that is presentable on a user interface of the computing device.

6. The computing device implemented method of claim 1, further comprising producing a graphical alert.

7. The computing device implemented method of claim 1, further comprising: providing the at least one detectable feature to the machine learning system for further training of the machine learning system.

8. A system comprising:
a computing device comprising:
a memory configured to store instructions; and
a processor to execute the instructions to perform operations comprising:
receiving data representing one or more images of dental information associated with a patient, the one or more images containing one or more unidentified image features of the patient;
adjusting the data representing the one or more images of dental information into a predefined format, wherein adjusting the data includes adjusting one or more visual parameters associated with the one or more images of dental information;
using a machine learning system based on one or more neural networks to determine one or more confidence scores for the presence of at least one detectable feature,
each of the one or more confidence scores corresponding to one or more distinct portions of the one or more images of dental information,
the at least one detectable feature representing at least one or more diseases, one or more prior procedures performed upon the patient, or one or more anatomical structure characteristics, and
the machine learning system being trained with dental imagery comprising one or more training images, wherein annotations of the one or more training images are provided by different annotators;
producing a representation based on the determined one or more confidence scores, the representation comprising information about
a presence or absence of the at least one detectable feature, and
a tooth number associated with the at least one detectable feature, if present, within the one or more images of dental information,
wherein the information in the produced representation is selectively presented based upon user input;
comparing the at least one detectable feature and patient data to represent a mapping and to represent a measure of a dental management system, and
generating a report comprising the at least one detectable feature.

9. The system of claim 8, wherein the operations further comprise: transferring the data representing the one or more images of dental information associated with the patient to one or more networked computing devices for statistical analysis.

10. The system of claim 8, wherein the machine learning system employs a convolution neural network.

11. The system of claim 8, wherein the at least one detectable feature includes a radiolucent lesion or an opaque lesion.

12. The system of claim 8, wherein the produced representation includes a graphical representation that is presentable on a user interface of the computing device.

13. The system of claim 8, wherein the operations further comprise producing a graphical alert.

14. One or more non-transitory computer readable media storing instructions that are executable by a processing device, and upon such execution cause the processing device to perform operations comprising:
receiving data representing one or more images of dental information associated with a patient, the one or more images containing one or more unidentified image features of the patient;
adjusting the data representing the one or more images of dental information into a predefined format, wherein adjusting the data includes adjusting one or more visual parameters associated with the one or more images of dental information;
using a machine learning system based on one or more neural networks to determine one or more confidence scores for the presence of at least one detectable feature,
each of the one or more confidence scores corresponding to one or more distinct portions of the one or more images of dental information,
the at least one detectable feature representing at least one or more diseases, one or more prior procedures performed upon the patient, or one or more anatomical structure characteristics, and
the machine learning system being trained with dental imagery comprising one or more training images, wherein annotations of the one or more training images are provided by different annotators;
producing a representation based on the determined one or more confidence scores, the representation comprising information about
a presence or absence of the at least one detectable feature, and
a tooth number associated with the at least one detectable feature, if present, within the one or more images of dental information,
wherein the information in the produced representation is selectively presented based upon user input;
comparing the at least one detectable feature and patient data to represent a mapping and to represent a measure of a dental management system, and generating a report comprising the at least one detectable feature.

15. The non-transitory computer readable media of claim 14, wherein the operations further comprise: transferring the data representing the one or more images of dental information associated with the patient to one or more networked computing devices for statistical analysis.

16. The non-transitory computer readable media of claim 14, wherein the machine learning system employs a convolution neural network.

17. The non-transitory computer readable media of claim 14, wherein the at least one detectable feature includes a radiolucent lesion or an opaque lesion.

18. The non-transitory computer readable media of claim 14, wherein the produced representation includes a graphical representation that is presentable on a user interface of the computing device.

19. The non-transitory computer readable media of claim 14, wherein the operations further comprise producing a graphical alert.

* * * * *